United States Patent [19]

Doherty

[11] Patent Number: 4,496,741
[45] Date of Patent: Jan. 29, 1985

[54] PROCESS FOR THE PREPARATION OF 5-AROYL-1,2-DIHYDRO-3H-PYRROLO[1,2-A]PYRROLE-1-CARBOXYLIC ACID DERIVATIVE

[75] Inventor: James B. Doherty, New Milford, N.J.

[73] Assignee: Merck & Co., Inc., Rahway, N.J.

[21] Appl. No.: 460,436

[22] Filed: Jan. 24, 1983

[51] Int. Cl.³ .......................................... C07D 487/02
[52] U.S. Cl. ................................................ 548/453
[58] Field of Search ......................................... 548/453

[56] References Cited

U.S. PATENT DOCUMENTS 4,089,969  4/1976  Carson ................................ 424/274

OTHER PUBLICATIONS

Badger et al., Aust. J. Chem., 17, pp. 1002–1013 (1964).
Dunn et al., Canadian J. of Chem.; 49, pp. 1032–1035 (1971).
Carson & Wong, J. Med. Chem., 16 (2), 172 to 175, (1973).

Primary Examiner—Glennon H. Hollrah
Assistant Examiner—D. B. Springer
Attorney, Agent, or Firm—Theresa Y. Cheng

[57] ABSTRACT

5-Aroyl-1,2-dihydro-3H-pyrrolo[1,2-a]pyrrole-1-carboxylic acid derivatives have been prepared from a 5-aroyl-7-hydroxycarbonyl-1,2-dihydro-3H-pyrrolo[1,2-a]pyrrole-1-carboxylic acid derivative via selective decarboxylation.

4 Claims, No Drawings

PROCESS FOR THE PREPARATION OF 5-AROYL-1,2-DIHYDRO-3H-PYRROLO[1,2-A]PYRROLE-1-CARBOXYLIC ACID DERIVATIVE

BACKGROUND OF THE INVENTION

This invention relates to an improved process involving decarboxylation. Specifically, it involves the preparation of 5-aroyl-1,2-dihydro-3H-pyrrolo[1,2-a]pyrrole-1-carboxylic acid derivatives via selective decarboxylation.

Decarboxylation via heterolytic cleavages generally fall into two catagories:

I. Decarboxylation of acids whose anions are less stable with respect to decarboxylation than the unionized acid; and II. Decarboxylation of acids whose unionized form is more susceptible to decarboxylation than their anions.

For most acids, decarboxylation (Catalogue I) takes place in a basic medium, i.e., in their anion forms. However, for α or β-keto acids, decarboxylation (Catalogue II) is usually carried out in an acidic medium, i.e., in their un-ionized free acid forms. 5-Aroyl-1,2-dihydro-3H-pyrrolo[1,2-a]pyrrole-1-carboxylic acids are useful anti-inflammatory agents of the structural formula (I).

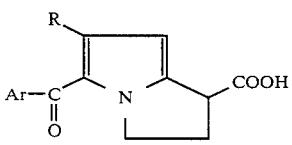

(I)

These compounds have been previously prepared in five steps (U.S. Pat. No. 4,089,969) as shown below:

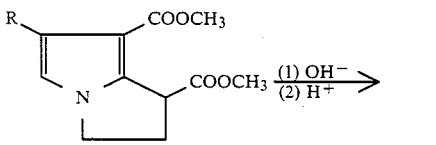

Step 1

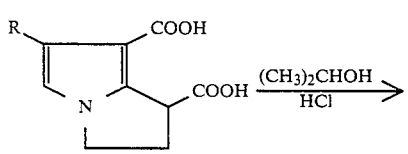

Step 2

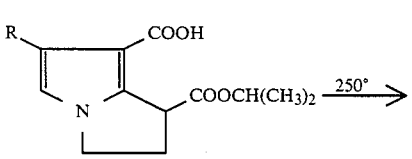

Step 3

(II)

Step 4

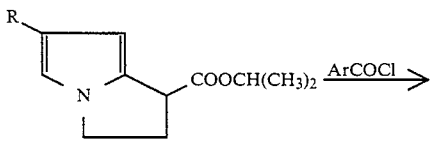

-continued

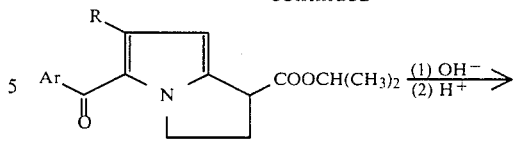

Step 5

(III)

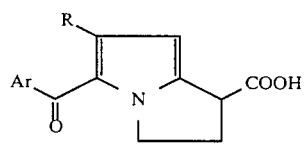

(I)

The prior art decarboxylation as described above is usually conducted at relatively high temperatures such as 250° C. To preserve selectivity of decarboxylation under the high temperatures, protection of the 1-carboxylic acid function becomes necessary. Accordingly, two extra steps, i.e., (a) the preparation of the monoester (II); and
(b) the hydrolysis of ester (III) to afford (I) are added to the process making it a 5-step process.

As expected, the overall yields of the prior art process are generally lower due to the additional steps and the drastic condition of the decarboxylation.

To the contrary, the present process relates to a selective decarboxylation whereby compounds of formula (I) are unexpectedly prepared from diacid (IV) under mild conditions, for example:

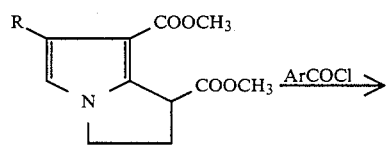

Step 1

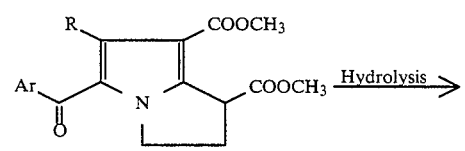

Step 2

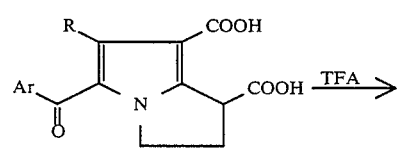

Step 3

(IV)

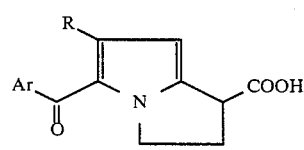

(I)

As shown above, the tedious blocking and deblocking steps are eliminated, and the drastic decarboxylation condition is avoided. Both contribute to the improved yield of compound (I).

DETAILED DESCRIPTION OF THE INVENTION

The present invention is concerned with a single-step process for preparing 5-aroyl-1,2-dihydro-3H-pyrrolo[1,2-a]pyrrole-1-carboxylic acid derivatives of the structural formula (I):

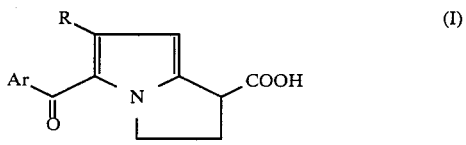

wherein
Ar is phenyl, $C_{1-4}$ alkylphenyl, $C_{1-4}$ alkoxyphenyl or halophenyl such as 4-methyl, 4-methoxy, 4-chloro, 4-fluoro, 3-chloro or 2-fluorophenyl preferably phenyl or 4-chlorophenyl; and
R is H; lower alkyl especially $C_{1-6}$ alkyl such as methyl, ethyl, n-propyl, butyl, pentyl or hexyl; or halo especially Cl, F, or Br; comprising acidic decarboxylation of a compound of the structural formula (V):

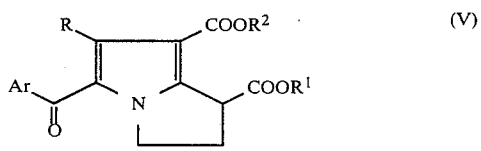

wherein Ar and R are as previously defined; and $R^1$ and $R^2$ independently are H, t-butyl, benzhydryl or other protecting groups which are easily removed in trifluoroacetic acid or other related organic acids.

The acidic decarboxylation is conducted under mild conditions. For example, 5-benzoyl-7-hydroxycarbonyl-1,2-dihydro-3H-pyrrolo[1,2-a]pyrrole-1-caboxylic acid is treated with refluxing trifluoroacetic acid to afford 5-benzoyl-1,2-dihydro-3H-pyrrolo[1,2-a]pyrrole-1-carboxylic acid. Other acids may also be used. For example, those listed below in Table I.

TABLE I

| Acids Used in the Decarboxylation |
|---|
| (1) An inorganic acid such as hydrochloric acid, sulfuric acid or p-toluene sulfonic acid. |
| (2) An organic acid of the structural formula: |

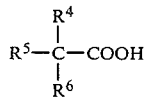

wherein $R^4$ and $R^6$ independently are hydrogen or halo such as iodo, bromo, chloro, or fluoro preferably chloro or fluoro; and
$R^5$ is H, $C_{1-6}$ alkyl, halo especially chloro or fluoro, or halo-$C_{1-6}$ alkyl such as trifluoromethyl, trichloromethyl, 1,1-difluoroethyl, or 1-chloro-1-fluoropropyl or the like.
(2) Preferred Acids:
Acetic acid;
Chloroacetic acid;
Chlorodifluoroacetic acid;
Dichloroacetic acid;
Difluoroacetic acid;
Trichloroacetic acid;
Pentafluoropropanoic acid;

TABLE I-continued

| Acids Used in the Decarboxylation |
|---|
| Trifluoroacetic acid; or a combination thereof. |

The decarboxylation may be conducted in an acid or in a inert solvent containing the acid. The solvents which are often used are illustrated below in Table II.

TABLE II

| Solvents for the Acidic Decarboxylation |
|---|
| Toluene |
| Benzene |
| Xylene |
| Tetrahydrofuran |
| 1,2-Dimethoxyethane |
| Dioxane |

The decarboxylation temperatures may vary with the acids or solvents being used. Usually the temperatures range from about 30° to about 120° C. Under the optimum conditions, i.e., in refluxing trifluoroacetic acid with or without solvent, the temperature ranges from about 35° to about 72° C.

Generally, the decarboxylation is substantially complete after heating at an appropriate temperature for about 1 to about 20 hours or under more favorable conditions, about 0.5 hours to about 5 hours.

The starting pyrrole diacids of the present process are prepared readily from the procedures disclosed in U.S. Pat. No. 4,089,969 and is incorporated herein by reference.

EXAMPLE 1

Decarboxylation of 5-benzoyl-7-hydroxycarbonyl-1,2-dihydro-3H-pyrrolo[1,2-a]pyrrole-1-carboxylic acid One mmole of 5-benzoyl-7-hydroxycarbonyl-1,2-dihydro-3H-pyrrolo[1,2-a]pyrrole-1-carboxylic acid is dissolved in 5 ml of trifluoroacetic acid and the resulting solution is heated at reflux for 1.5 hours. After most of the solvent is removed in vacuo, the residue is treated with 10 ml. of water. The resulting residue is filtered and dried in vacuo to give 5-benzoyl-1,2-dihydro-3H-pyrrole[1,2-a]pyrrole-1-carboxylic acid.

EXAMPLE 2

Decarboxylation of t-butyl 5-(p-fluorobenzoyl)-7-t-butoxycarbonyl-1,2-dihydro-3H-pyrrolo[1,2-a]pyrrole-1-carboxylate t-Butyl-5-(p-fluorobenzoyl)-7-t-butoxycarbonyl-1,2-dihydro-3H-pyrrolo[1,2-a]pyrrole-1-carboxylate (1 mmole) is dissolved in 5 ml of trifluoroacetic acid. The reaction mixture is heated at reflux for 5 hours before it is evaporated in vacuo to remove most of the solvent. The resulting oil is triturated with about 10 ml of water, filtered and dried in vacuo to afford 5-(p-fluorobenzoyl)-1,2-dihydro-3H-pyrrolo[1,2-a]pyrrole-1-carboxylic acid.

What is claimed is:
1. A process for preparing 5-aroyl-1,2-dihydro-3H-pyrrolo[1,2-a]pyrrole-1-carboxylic acid derivatives of the structural formula:

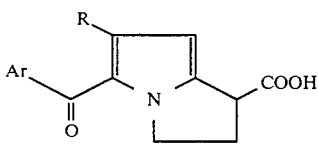

wherein Ar is phenyl, $C_{1-4}$alkylphenyl, $C_{1-4}$alkoxyphenyl or halophenyl; R is H, $C_{1-4}$alkyl or halo comprising decarboxylating a diacid derivatives of the structural formula:

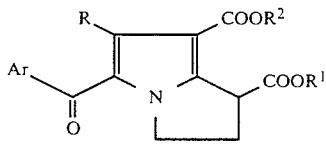

where R and Ar are as previously defined; and $R^1$ and $R^2$ independently are H, t-butyl, or benzhydryl in an acid selected from the group consisting of trifluoroacetic acid and trichloroacetic acid or a combination thereof.

2. The process of claim 1 wherein the acid is trifluoroacetic acid.

3. The process of claim 1 wherein the diacid derivative is 5-benzoyl-7-hydroxycarbonyl-1,2-dihydro-3H-pyrrolo[1,2-a]pyrrole-1-carboxylic acid.

4. The process of claim 1 wherein the diacid derivative is t-butyl-5-benzoyl-7-t-butoxycarbonyl-1,2-dihydro-3H-pyrrolo[1,2-a]pyrrole-1-carboxylate.

* * * * *